United States Patent [19]

DiGiorgio et al.

[11] Patent Number: Plant 7,307

[45] Date of Patent: Aug. 28, 1990

[54] CARNATION NAMED DIGISUN

[75] Inventors: Antonio DiGiorgio; Renato DiGiorgio, both of San Remo, Italy

[73] Assignee: Laboratoire de Physiologie Vegetale, La Londe-Les-Maures, France

[21] Appl. No.: 294,518

[22] Filed: Dec. 21, 1988

[51] Int. Cl.[5] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

A new standard carnation cultivar particularly distinguished by its very large, light yellow colored flowers of a shade between Dresden Yellow and Sulphur Yellow, the flower petals being striated with very thin stripes of a medium Neyron Rose color giving the bloom a very distinctive appearance. The blooms are carried on strong, upright and rigid stems averaging about 90 cm. in length of a plant having moderately abundant foliage and standing at an average height of about 104 cm. at eight months. This plant blooms profusely, at recurrent intervals, in the Spring, Midseason and Fall blooming seasons, and on the plant, the flowers hang on and dry. As cut flowers, the lasting quality is at least ten days in vase keeping which, together with the other favorable characteristics of this new variety, provides a plant of very favorable marketing advantages.

1 Drawing Sheet

BACKGROUND OF THE NEW PLANT

Our new carnation cultivar originated as a seedling of a hybrid developed by us in our nursery in San Remo, Italy, where we do business under the name Azienda Agricola Di Giorgia Antonio E. Renate, the said hybrid resulting from our crossing two carnation varieties selected from our collection of carnation varieties identified and maintained at our nursery for breeding purposes. The present seedling was selected from among a group resulting from planting seeds of the before mentioned hybrid and this selected seedling was propagated by us and under our direction at our San Remo nursery by means of cuttings with such satisfactory results that propagation of this new plant was carried on through several successive generations at San Remo, which proved conclusively that the novel characteristics of this new plant would be retained from generation to generation and thus homogeneity could be assured.

The plant is now being propagated on a commercial scale at Establissements Barberet et Blanc, Laboratoire de Physiologie Vegetale, 83250 La Londe-Les Maures, France.

DESCRIPTION OF THE DRAWING

Our new carnation cultivar is illustrated by the accompanying photographic drawing, which shows several stems of the plant with buds and blooms in several stages of development, the color rendition being as nearly true as is reasonably possible to obtain by professional photographic procedures.

DESCRIPTION OF THE NEW PLANT

The following is a detailed description of our new standard carnation variety based upon observation of plants grown in greenhouse, as well as outdoors, at San Remo, Italy, and at La Londe-Les Maures, France, the color designations stated herein being according to The R.H.S. Colour Chart published by The Royal Horticultural Society of London, England.

THE PLANT

Origin: Seedling.

Parentage:

*Seed parent.*—Variety No. 75 (unpatented).

*Pollen parent.*—Variety No. 262 (unpatented). Both varieties are identified in our breeding records maintained at our nursery at Via Villetta 41, 18038 San Remo, Italy.

Classifications:

*Botanic.*—*Dianthus caryophyllus.*

*Commercial.*—Standard carnation.

Form: Bush; erect and rigid and having at least four stems emitted near the ground.

Height: Average about 104 cm. at four months.

Main Stem Length: Less than 15 cm. due to pinching.

Growth: Vigorous, upright and rigid.

Branching Character: This plant has average branching.

Foliage:

*Quantity.*—Moderately abundant.

*Number of leaves.*—More than 120.

*Leaf size.*—Averages about 12.5 cm. long and 1 cm. wide, at the seventh node.

*Leaf shape.*—Oblong with curved margins.

*Texture.*—Leathery.

*Ribs and veins.*—Hardly noticeable.

*Rachis.*—Hardly noticeable.

*Color.*—Upper side and under side, between 189-A and 147-A.

*Leaflets.*—None.

THE BUD

Size: Large.

*Diameter.*—Averages about 2.6 cm.

*Length.*—Averages about 2.6 cm.

Shape: Ovoid.

Opening rate: Normal.

Color of Petals: When sepals first divide, between 5-C and 6-D. When petals begin to unfurl, between 5-C and 6-D with 55-C striations beginning to appear.

Sepals:

*Number.*—Five.

*Shape.*—Rather ovate but joined together at the lower parts and having an acumiante apex.

*Character.*—At the beginning, the sepals are hooded over the bud and as the flower opens, the sepals curl back.

*Color.*—Inside, 145-C. Outside, 145-B/143-C.

*Striae.*—Longitudinal.

Calyx:

*Shape.*—Funnel-shaped.

*Size.*—Large.

*Aspect.*—Smooth.

*Splitting.*—Very little.

Flower stem:

*Length.*—Averages about 90 cm.

*Character.*—Erect and rigid.

*Color.*—Between 189-A and 147-A.

THE FLOWER

Blooming habit: Recurrent, blooming profusely in the Spring, Midseason and Fall blooming periods with a tendency to give few blooms in the Fall.

Size of flower: Very large.

*Diameter.*—Averages about 8.5 cm.

*Depth.*—Averages about 5.5 cm.

Borne: Singly on long, erect and strong stems.

Shape: When bloom first opens, high-centered. When bloom matures, dome-shaped.

Petalage:

*Number of petals.*—Average about 102.

*Arrangement.*—Imbricated.

*Form.*—Fan-shaped with rounded edges and deeply serrated apex.

*Texture.*—Leathery.

*Aspect.*—Satiny.

*Color.*—Both inside and outside petals: Body — Between 5-C and 6-D with straie of 55-C and 55-D. Base — Greenish White. Reverse side — 6-D with the inside of the petals having thin striae of 55-D.

*Petaloids.*—Number: Less than eight. Size: Smaller than the petals. Color: The same as the petals.

Flower stem:

*Length.*—Averages about 90 cm. Cut at the tenth node.

*Chararacter.*—Upright with good strength.

*Color.*—Between 147-A and 189-A.

Fragrance: Perceptible.

Discoloration after full bloom: Very little.

Persistence: The flowers hang on and dry.

Lasting quality: As a cut flower, at least ten days in vase keeping.

THE REPRODUCTIVE ORGANS

Stamens:

*Number.*—Six to twelve.

*Arrangement.*—Encircling the ovary.

*Anthers.*—Size: Less than 4 mm. Color: Yellowish.

*Filaments.*—Length: Average about 3 cm. Color: Yellow.

Pistils:

*Number.*—Two.

*Styles.*—Length: Averages about 2.5 cm. Color: Yellow.

*Stigma.*—Color: Slightly pink.

Character of ovaries: Ribbed.

We claim:

1. The new and distinctive carnation cultivar substantially as herein shown and described, particularly characterized by the very large size of its light yellow colored blooms which have numerous petals with light red striae, the flowers being produced profusely at recurrent periods during the blooming season on long, strong and erect stems having moderately abundant foliage.

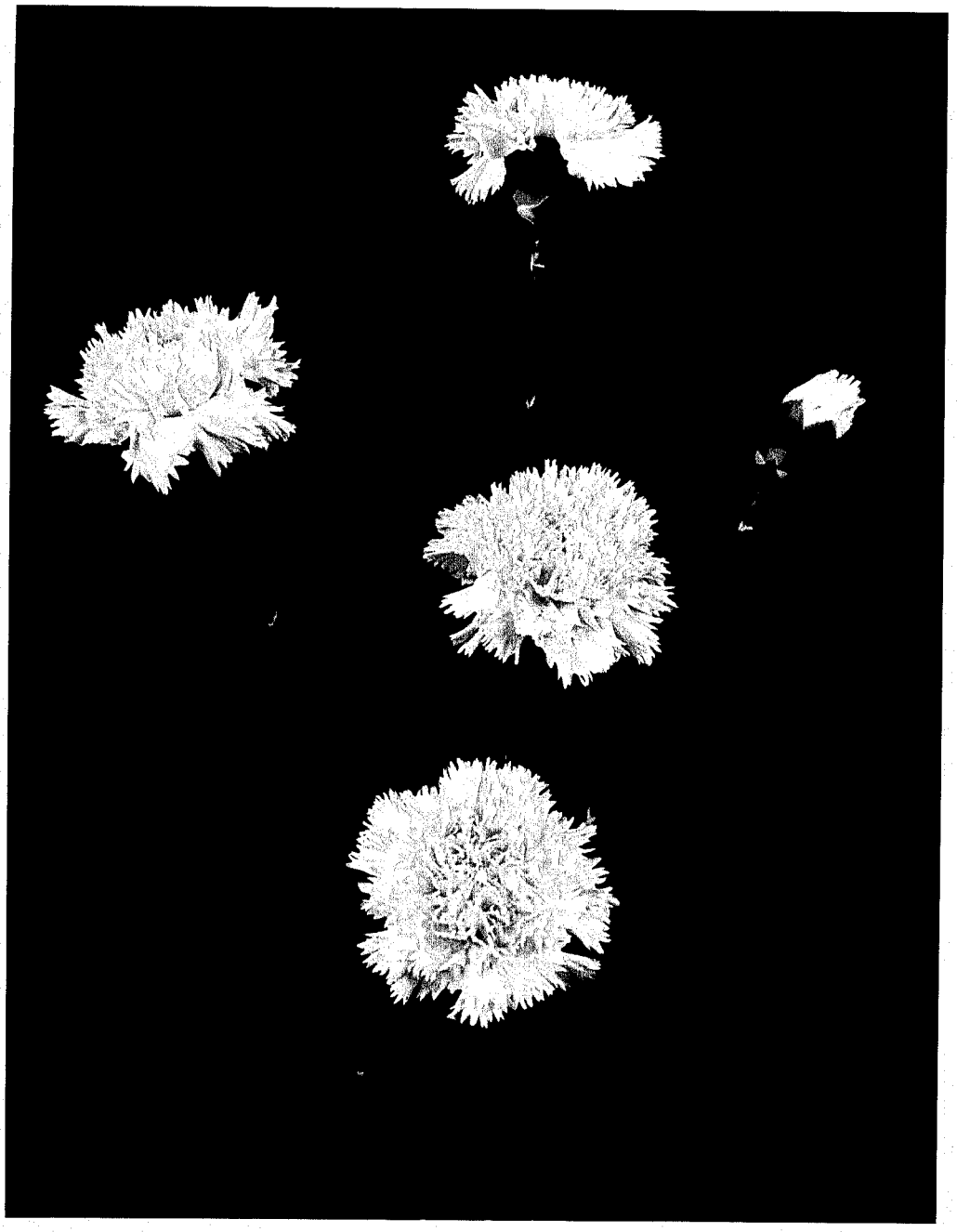

* * * * *